(12) United States Patent
Kimmel et al.

(10) Patent No.: US 12,064,571 B2
(45) Date of Patent: Aug. 20, 2024

(54) SYSTEMS AND METHODS FOR PROVIDING A STEERABLE SHEATH WITH IMPROVED TORQUE TRANSFER DURING DEFLECTION

(71) Applicant: Imricor Medical Systems Inc., Burnsville, MN (US)

(72) Inventors: Scott Kimmel, St. Paul, MN (US); Shawn J. Noble, Lakeville, MN (US); Meng Chang, Inver Grove Heights, MN (US); Steven R. Wedan, Savage, MN (US)

(73) Assignee: Imricor Medical Systems Inc., Burnsville, MN (US)

( * ) Notice: Subject to any disclaimer, the term of this patent is extended or adjusted under 35 U.S.C. 154(b) by 0 days.

(21) Appl. No.: 18/449,421

(22) Filed: Aug. 14, 2023

(65) Prior Publication Data
US 2024/0050701 A1 Feb. 15, 2024

Related U.S. Application Data

(60) Provisional application No. 63/397,712, filed on Aug. 12, 2022.

(51) Int. Cl.
*A61M 25/01* (2006.01)
(52) U.S. Cl.
CPC ............... *A61M 25/0147* (2013.01)

(58) Field of Classification Search
CPC .......... A61M 25/0105; A61M 25/0133; A61M 25/0147; A61M 2025/015
See application file for complete search history.

(56) References Cited

U.S. PATENT DOCUMENTS 5,571,085 A 11/1996 Accisano
2010/0168827 A1 7/2010 Schultz

OTHER PUBLICATIONS

International Search Report and Written Opinion issued on Jan. 23, 2024 in PCT/23/72160 (15 pages).

*Primary Examiner* — Laura A Bouchelle
(74) *Attorney, Agent, or Firm* — Fox Rothschild LLP; Carol E. Thorstad-Forsyth

(57) ABSTRACT

Systems and methods for operating steerable sheath (SS). The methods comprise: causing an inner shaft (IS) to move in a first direction (FD) relative to an outer shaft (OS) having a first lumen (FL) in which IS is disposed; applying tension to a first pull wire (FPW) as IS moves in FD (FPW being partially disposed in a wall of IS and in FL of OS, FPW's first end being connected to IS and FPW's second end being connected to OS); allowing a deflectable region of IS's wall to transition from a straight state to a deflected state as tension is applied to FPW; causing IS to move in a second direction relative to OS; removing the tension being applied to FPW as IS moves in the second direction; and allowing the deflectable region of IS's wall to return to the straight state as tension is being removed from FPW.

38 Claims, 10 Drawing Sheets

SYSTEMS AND METHODS FOR PROVIDING A STEERABLE SHEATH WITH IMPROVED TORQUE TRANSFER DURING DEFLECTION

CROSS-REFERENCE TO RELATED APPLICATION

The present applications claims priority to and the benefit of U.S. Provisional Patent Application 63/397,712 which was filed on Aug. 12, 2022. The entire content of the Provisional Application is incorporated herein by reference.

BACKGROUND

Statement of the Technical Field

The present disclosure relates generally to medical devices. More particularly, the present disclosure relates to implementing systems and methods for providing a steerable sheath with improved torque transfer during deflection. The steerable sheath can be used in medical procedures along with cardiac ablation catheters, endomyocardial ablation catheters and/or other medical equipment.

Description of the Related Art

Methods for manufacturing steerable sheaths are known. Most steerable sheaths utilize the same basic construction scheme in which one or more pull wires are disposed within the wall of the sheath and the inner lumen is left open so that a catheter or other device can pass through the sheath. The major limitation of this design is that when the sheath is deflected, one side of the sheath becomes compressed. When the deflected sheath is passed through a tortuous or curved anatomy, the lowest energy state is for the compressed side of the shaft to locate on the inner side of the curved path. Therefore, the sheath has a mechanical bias to this state, and when an attempt is made to rotate the sheath shaft such that the compressed curve is on the outside of the curve, the sheath will quickly rotate back into the lowest energy state with the compressed side of the sheath on the inside of the curve. Clinically, the physicians describe this phenomenon as sheath "whip" or "flip over". In practical terms, sheath whip limits the number of locations that can be reached by a catheter when delivered through the sheath.

SUMMARY

The present disclosure concerns systems and methods for operating a steerable sheath during a medical procedure. The methods comprise: causing an inner shaft of the steerable sheath to move in a first direction relative to an outer shaft having a first lumen in which the inner shaft is at least partially disposed; applying tension to a first pull wire as the inner shaft moves in the first direction (wherein the first pull wire is partially disposed in a wall of the inner shaft and partially disposed in the first lumen of the outer shaft, a first end of the first pull wire is connected to the inner shaft, and a second end of the first pull wire is connected to the outer shaft); allowing a deflectable region of the inner shaft's wall to transition from a straight state to a deflected state as the tension is being applied to the first pull wire; causing the inner shaft of the steerable sheath to move in a second opposing direction relative to the outer shaft; removing the tension being applied to the first pull wire as the inner shaft moves in the second opposing direction; allowing the deflectable region of the inner shaft's wall to return to the straight state as the tension is being removed from the first pull wire; and/or using the steerable sheath to deliver a device to a location inside a body of a living thing during the medical procedure. The device is movably disposed in a second lumen of the inner shaft.

A material of the deflectable region of the inner shaft may have a durometer that is lower than a durometer of a material of a remaining portion of the inner shaft such that the remaining portion of the inner shaft remains in a straight state throughout use of the steerable sheath. The first pull wire may extend only a portion of an entire length of the inner shaft that comprises at least the deflectable region.

The applying tension to a first pull wire may comprise changing a location of a first point where the first pull wire exits the inner shaft's wall relative to a second point where the second end of the first pull wire is connected to the outer shaft. The second point may have a static location relative to the outer shaft throughout use of the steerable sheath.

Additionally or alternatively, the applying tension to a first pull wire may comprise changing a distance between a first point where the first pull wire exits the inner shaft's wall relative to a second point where the second end of the first pull wire is connected to the outer shaft.

The methods may also comprise: using the first pull wire to prevent compression of the inner shaft and the outer shaft while the deflectable region transitions to the deflected state; using a flexible compliant member to seal a space between the inner shaft and the outer shaft (wherein the flexible compliant member extends between the inner shaft and the outer shaft); allowing the flexible compliant member to deform as the inner shaft moves in the first direction and tension is being applied to the first pull wire; using the flexible compliant member to prevent the first pull wire from contacting blood of an individual to which the medical procedure is being performed; and/or using the flexible compliant member to facilitate provision of a chemical substance in a space between the inner shaft and the outer shaft.

Additionally or alternatively, the methods may also comprise allowing slack in a second pull wire when the tension is being applied to the first pull wire (wherein the second pull wire is partially disposed in the wall of the inner shaft and partially disposed in the first lumen of the outer shaft, a first end of the second pull wire is connected to the inner shaft, and a second end of the second pull wire is connected to the outer shaft). A point at which the second pull wire is coupled to the outer shaft is closer to the deflectable region of the inner shaft's wall than a point at which the first pull wire is coupled to the outer shaft. The second pull wire extends through the deflectable region of the inner shaft's wall. The methods may further comprise applying tension to the second pull wire as the inner shaft moves in the second opposing direction. The first and second pull wires may have a same length or different length. The second pull wire may extend an entire length of the inner shaft.

The causing the inner shaft of the steerable sheath to move in the first direction may comprise applying a pushing force to a knob of a handle assembly coupled to the steerable sheath. The methods may also comprise: adjusting an amount of sliding friction between the inner shaft and the knob via manipulation of a valve disposed in the knob; and/or an amount of force required for causing deflection of the deflectable region of the inner shaft's wall via manipulation of a valve disposed in the knob.

The present document also concerns a steerable sheath. The steerable sheath comprises: an outer shaft having a first lumen; an inner shaft at least partially disposed in the first lumen, configured to move in a first direction relative to an outer shaft, and configured to move in a second opposing direction relative to the outer shaft; and a first pull wire configured to have tension applied thereto as the inner shaft moves in the first direction. The first pull wire is partially disposed in a wall of the inner shaft and partially disposed in the first lumen of the outer shaft. A first end of the first pull wire is connected to the inner shaft. A second end of the first pull wire is connected to the outer shaft. A deflectable region of the inner shaft's wall is transitionable from a straight state to a deflected state as the tension is being applied to the first pull wire. The deflectable region of the inner shaft's wall is configured to return to the straight state as the tension is being removed from the first pull wire when the inner shaft moves in the second opposing direction.

The steerable sheath may be configured to deliver a device to a location inside a body of a living thing during a medical procedure, wherein the device is movably disposed in a second lumen of the inner shaft. A material of the deflectable region of the inner shaft may have a durometer that is lower than a durometer of a material of a remaining portion of the inner shaft such that the remaining portion of the inner shaft remains in a straight state throughout use of the steerable sheath.

The first pull wire may extend only a portion of an entire length of the inner shaft that comprises at least the deflectable region. The first pull wire may be configured to prevent compression of the inner shaft and the outer shaft while the deflectable region transitions to the deflected state. The tension may be applied to the first pull wire by: changing a location of a first point where the first pull wire exits the inner shaft's wall relative to a second point where the second end of the first pull wire is connected to the outer shaft; and/or changing a distance between a first point where the first pull wire exits the inner shaft's wall relative to a second point where the second end of the first pull wire is connected to the outer shaft. The second point may have a static location relative to the outer shaft throughout use of the steerable sheath.

The steerable sheath may also comprise a flexible compliant member configured to seal a space between the inner shaft and the outer shaft. The flexible compliant member extends between the inner shaft and the outer shaft. The flexible compliant member may also be configured to: deform as the inner shaft moves in the first direction and tension is being applied to the first pull wire; prevent the first pull wire from contacting blood of an individual to which a medical procedure is being performed; and/or facilitate provision of a chemical substance in a space between the inner shaft and the outer shaft.

The steerable sheath may further comprise a second pull wire that is configured to have slack when the tension is being applied to the first pull wire. The second pull wire is partially disposed in the wall of the inner shaft and partially disposed in the first lumen of the outer shaft. A first end of the second pull wire is connected to the inner shaft. A second end of the second pull wire is connected to the outer shaft. A point at which the second pull wire is coupled to the outer shaft is closer to the deflectable region of the inner shaft's wall than a point at which the first pull wire is coupled to the outer shaft. The second pull wire extends through the deflectable region of the inner shaft's wall. Tension is applied to the second pull wire as the inner shaft moves in the second opposing direction.

The first and second pull wires may have a same length or different length. The second pull wire may extend an entire length of the inner shaft. Movement of the inner shaft in the first direction may be caused by applying a pushing force to a knob of a handle assembly coupled to the steerable sheath. An amount of sliding friction between the inner shaft and the knob may be adjustable via manipulation of a valve disposed in the knob. An amount of force required for causing deflection of the deflectable region of the inner shaft's wall may be adjustable via manipulation of a valve disposed in the knob.

BRIEF DESCRIPTION OF THE DRAWINGS

The present solution will be described with reference to the following drawing figures, in which like numerals represent like items throughout the figures.

Figure 1:
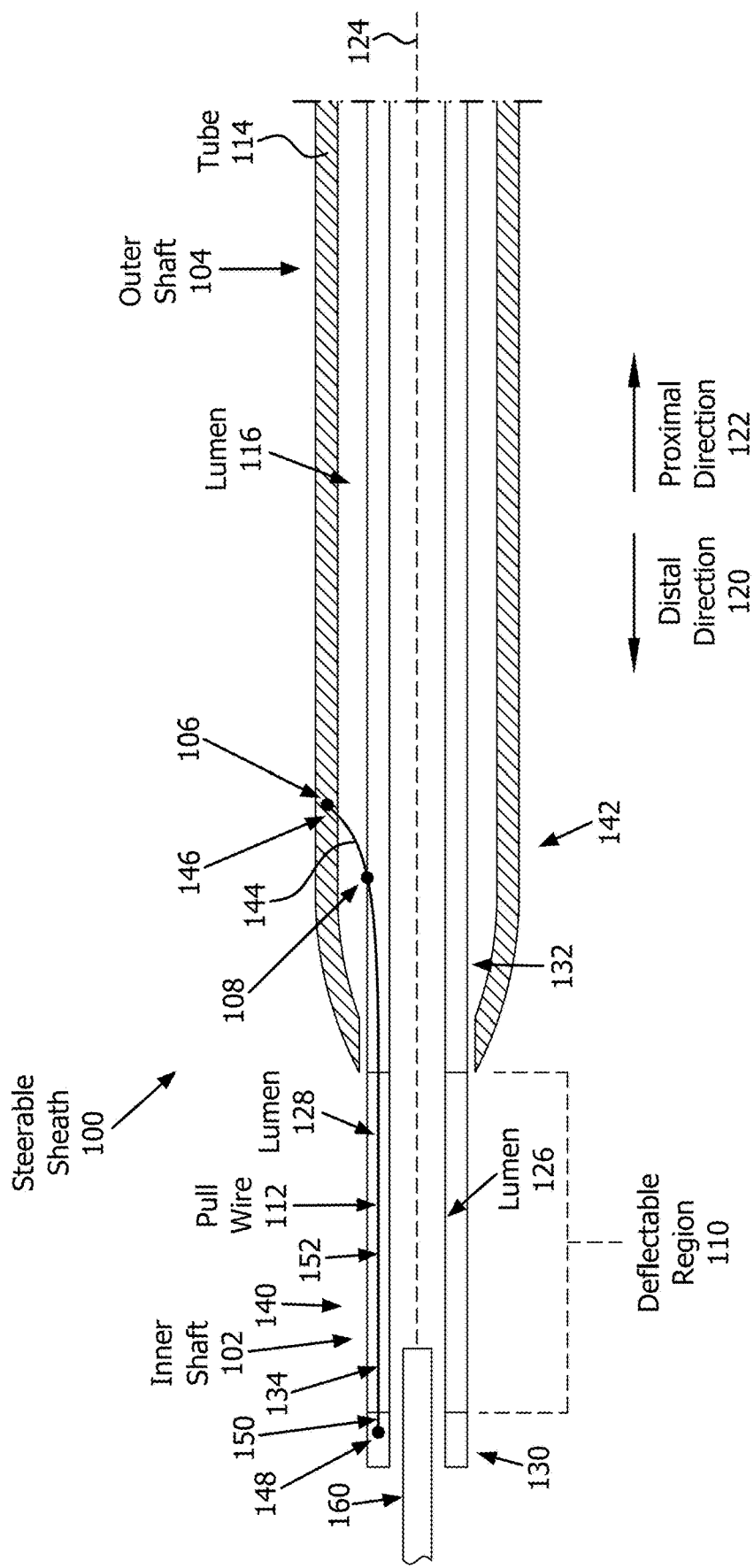
FIGS. 1-2 provide illustrations of a steerable sheath in accordance with the present solution.

The dimensions shown in the figures are by way of example only; other sizes and shapes of various components may be used.

DETAILED DESCRIPTION

Reference will now be made to the embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to a person skilled in the relevant art and having possession of this disclosure, are to be considered within the scope of the invention.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to." Definitions for additional terms that are relevant to this document are included at the end of this Detailed Description.

In this document, when terms such as "first" and "second" are used to modify a noun, such use is simply intended to distinguish one item from another, and is not intended to require a sequential order unless specifically stated. In addition, terms of relative position such as "vertical" and "horizontal", or "front" and "rear", when used, are intended to be relative to each other and need not be absolute, and only refer to one possible position of the device associated with those terms depending on the device's orientation.

Unless defined otherwise, all technical and scientific terms used in this document have the same meanings as commonly understood by one of ordinary skill in the art.

There remains a need to provide a steerable sheath that can be deflected and rotated without the occurrence of this whipping phenomenon and consequently allow for more locations to be reached with catheters and other devices delivered through the sheath. The present solution provides such a steerable sheath. The sheath comprises an inner shaft and outer shaft that are connected via a pull wire just distal of the inner shaft deflectable region.

Referring now to FIG. 1, there is provided an illustration of a steerable sheath 100 in accordance with the present solution. Steerable sheath 100 comprises an inner shaft 102 and an outer shaft 104. The inner shaft 102 and outer shaft 104 are both elongated members formed of flexible material(s). The flexible material(s) can include, but is(are) not limited to, a poly ether block amide (for example, such as PEBAX) and/or another polymer. The outer shaft 104 comprises a tube 114 with a lumen (or channel) 116. The inner shaft 102 moves in two opposing directions 120, 122 along a central axis 124 of the outer shaft 104.

The inner shaft 102 comprises a main lumen 126 and pull wire lumen(s) 128. The main lumen 126 is configured to facilitate delivery of a catheter or other device to a given location inside a body of an individual. In this regard, the main lumen 126 of the inner shaft 102 is designed to allow the catheter 160 or other device to slidingly travel therethrough. The catheter 160 comprises a flexible tube to be inserted into an opening formed in a body cavity (for example, a bladder of a human or other animal) for supply of fluid (for example, a liquid medicine) thereto or removal of fluid (for example, urine) therefrom.

The inner shaft 102 has a deflectable region 110 located at a proximal end 140 thereof. Proximal end 140 is distal to a distal opening (not shown in FIG. 1) of the outer shaft 104. The deflectable region 110 at least partially extends out of a proximal end 142 of the outer shaft 104. The deflectable region 110 is formed of a material that is more flexible than the material used to form other portions 130, 132 of the inner shaft. The material used for the deflectable region 110 can include, but is not limited to, a relatively low durometer polymer. At least a portion of the deflectable region 110 comprises a thin wall tubing and a braid or coil to eliminate any stress risers created from deflection of the device.

The pull wire lumen(s) 128 is(are) provided in the wall of the main lumen 126. A pull wire 134 is disposed in each pull wire lumen 128. The pull wire 134 has two opposing ends 146, 148 and a main body 152. End 148 of the pull wire 134 is coupled to the inner lumen 128 at point 150. Point 150 resides outside of a deflectable region 110 of the inner shaft's wall. Point 150 is located adjacent to or in proximity to the deflectable region 110 of the inner shaft's wall. For example, point 150 is located within N centimeters of the deflectable region 110, where N is any number (integer or decimal) greater than zero and less than five. The present solution is not limited to the particulars of this example. The distance between point 150 and the deflectable region 110 can be selected in accordance with any given application of the steerable sheath.

The main body 152 of the pull wire 134 extends through the deflectable region 110 and exits the inner shaft 102 at a point 108. Point 108 resides outside of a deflectable region 110 of the inner shaft's wall. Point 108 is located adjacent to or in proximity to the deflectable region 110. The distance between point 108 and deflectable region 110 can be the same as or different than the distance between point 150 and the deflectable region 110.

A portion 144 of the pull wire's main body extends out from the inner shaft 102 and through the lumen 116 to the outer shaft 104. A second end 146 of the pull wire 134 is attached to the outer shaft 104 at anchor point 106. Hence, the pull wire 134 connects the two shafts 102, 104 to each other at a point near or otherwise close to the deflectable region 110 of the inner shaft's wall.

Figure 2:
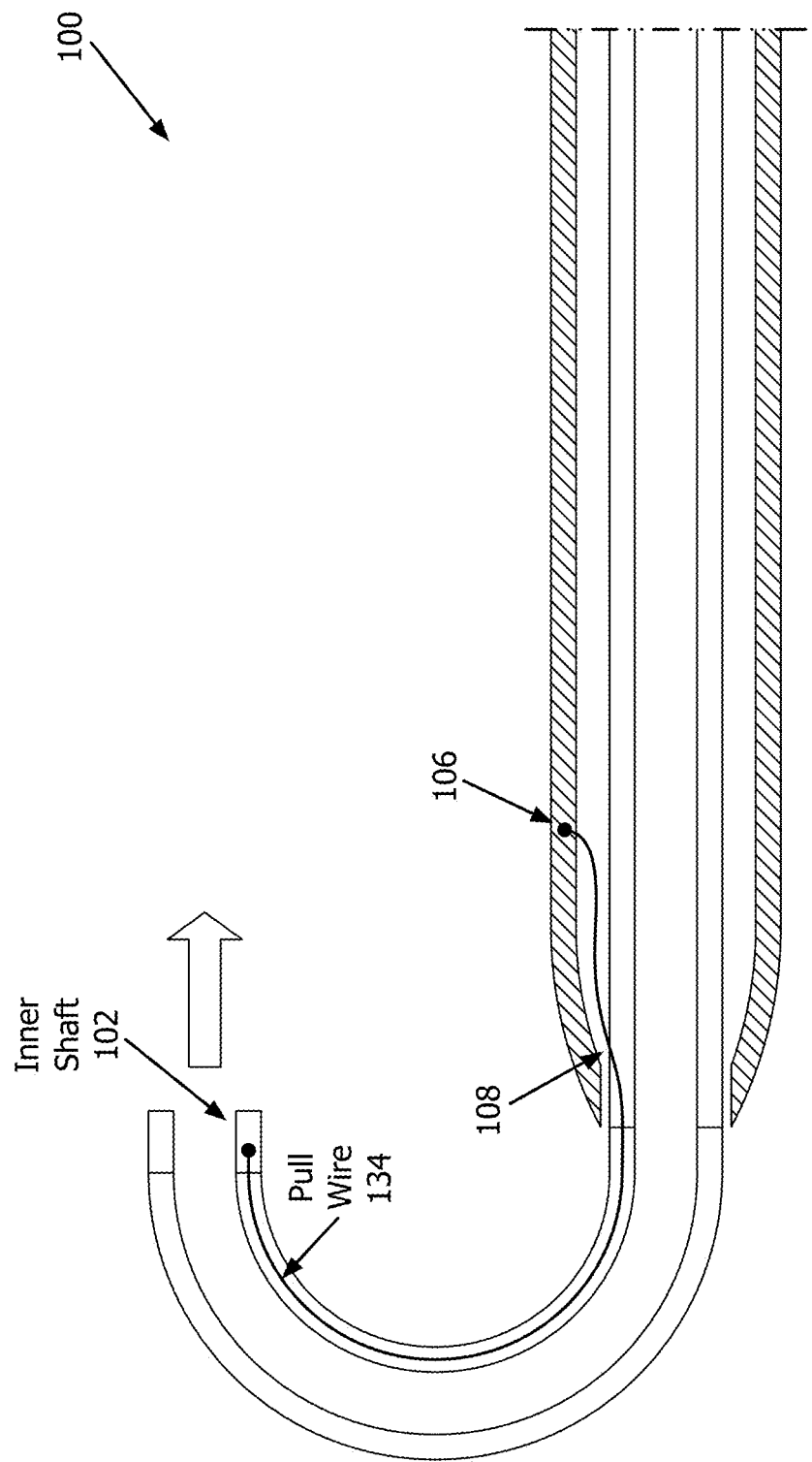

When the inner shaft 102 moves in the distal direction 120 in relation to the outer shaft 104, tension is applied to the pull wire 134 because the location of the anchor point 106 does not change relative to the outer shaft 104 but the location of the exit point 108 does change relative to the outer shaft 104 as a result of the inner shaft's movement. The change in location of the exit point 108 causes an increase in the exit point's distance from the anchor point 106. The tension causes the deflectable region 110 to deflect and bend as shown in FIG. 2. When the inner shaft 102 returns to its original straight position (or state), the tension on the pull wire 134 is released. The deflectable region 110 returns to its straight position (or state) when release of the tension occurs.

The advantage of this steerable sheath design is that the pull wire's lumen 128 does not traverse the entire length of the inner shaft 102, but rather a portion of the inner shaft 102 comprising the deflectable region 110. Therefore, when the sheath is deflected, no portion of the inner or outer sheath shaft wall is compressed in the regions that would pass through tortuous anatomy and lead to the whipping or turnover phenomenon that occurs in sheaths created with the standard design.

In some scenarios, the pull wire 134 is formed of a biocompatible material. Such biocompatible materials include, but are not limited to, a Polyether-Ether-Ketone (PEEK) material, a Nitinol Titanium (NiTi) based material, and/or a material used for medical sutures (for example, nylon, polypropylene, and/or Ultra-High-Molecular-Weight-Polyethylene (UHMWPE)), and/or a biocompatible metal (for example, stainless steel). The pull wire 134 can comprise a single wire or a plurality of wires (for example, braided wires).

Figure 3:
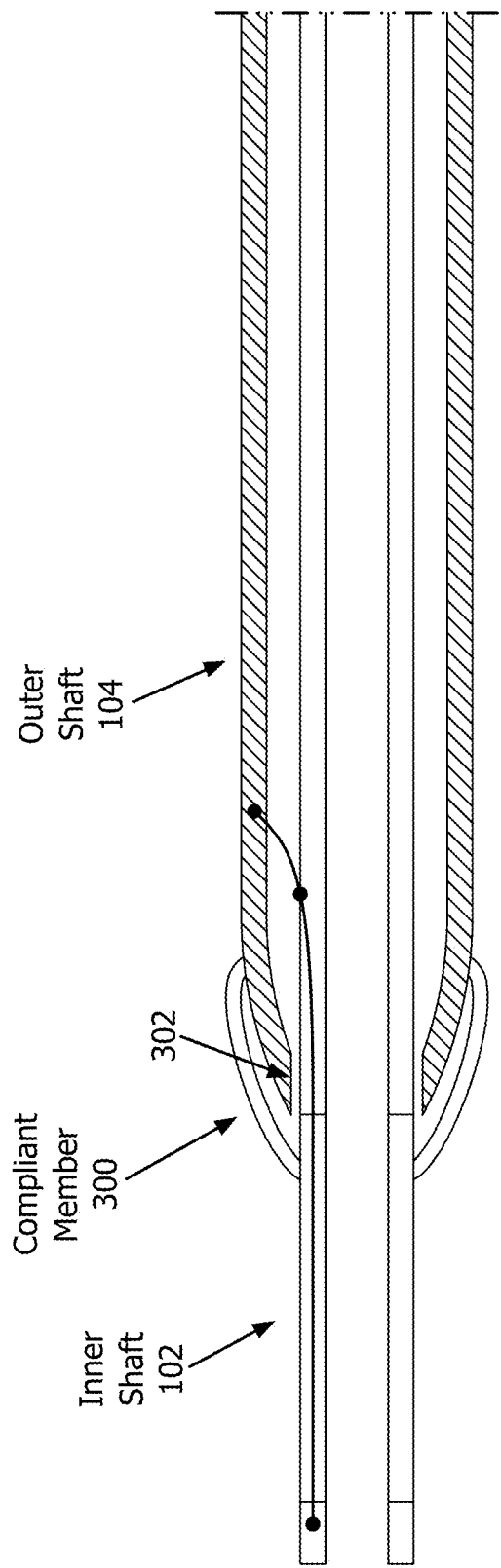
FIGS. 3-4 provide illustrations of another steerable sheath with a compliant member.
Figure 4:
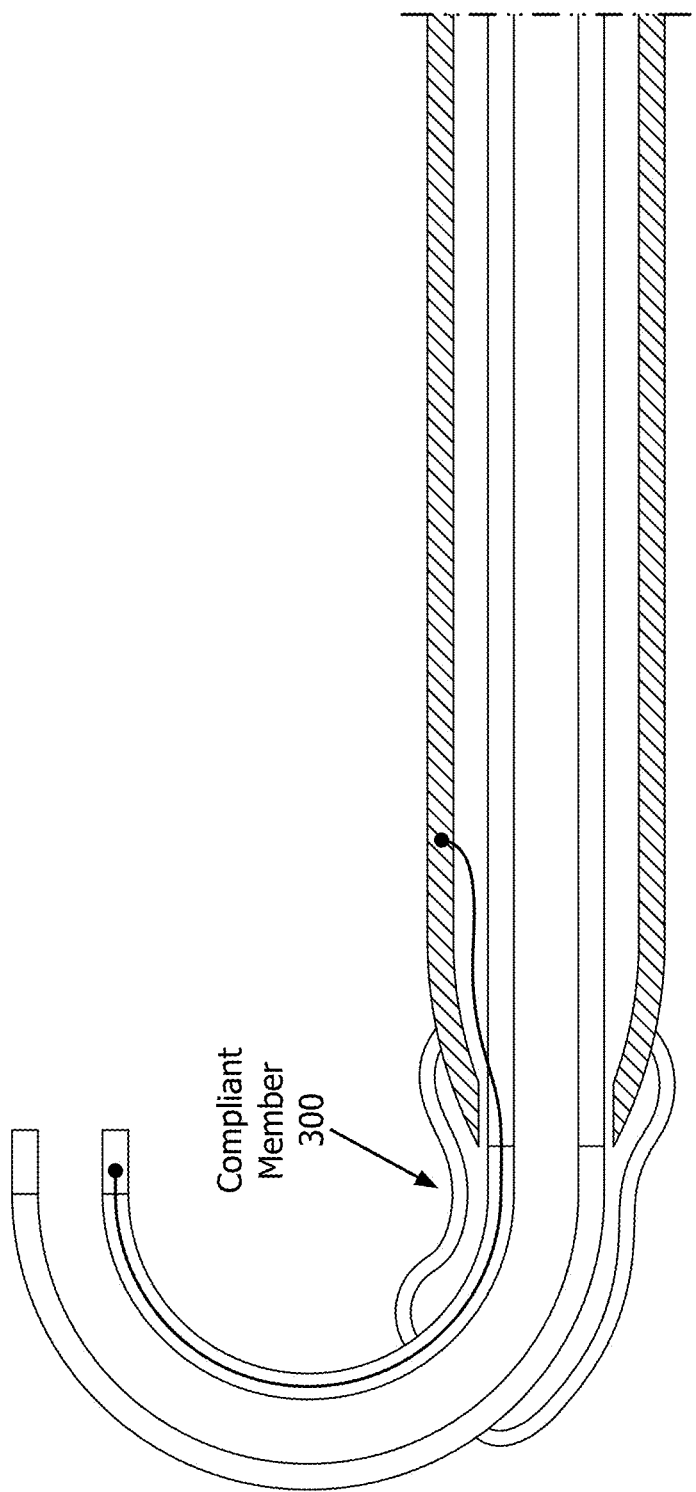

In those or other scenarios, the steerable sheath can also comprise a compliant member 300 as shown in FIGS. 3-4. The compliant member 300 can include, but is not limited to, a silicone balloon or other flexible member. The compliant member 300 is coupled to both the inner and outer shafts such that it extends between the shafts and seals a space 302 between the shafts. The compliant member 300 deforms when the inner shaft is slidingly moved in and out of the outer shaft. This design prevents the pull wire material from contacting the patient's blood and eliminates the need for the pull wire to be composed of a biocompatible material.

A potential advantage of integrating the compliant member 300 between the outer and inner shafts is the creation of opportunities to visualize the sheath shafts. In one scenario, an agent, contrast media (for example, a Gadolinium contrast media), dye and/or other chemical substance could be injected into the space 302 between the two shafts. This could be done without the presence of the compliant member 300. However, a constant contrast injection process is need which is more costly and complex.

In those or other scenarios, transmission line(s) could be placed in the space 302 between the two shafts and/or a receive coil could be positioned in the wall(s) of the inner or outer shaft(s). Tracking coils are used as locators within the MRI environment to determine the exact x,y,z location of those coils, and hence the device. This is unique to the MM environment. These devices are not typically visible in MR images like they would be in fluoroscopy images, so this is a way to track these devices. The transmission line is used to transmit these tracking coil signals to the MRI scanner for later use to determine the device's location in MR space.

In those or other scenarios, the steerable sheath can comprise other component(s) to facilitate the inner shaft's return to its undeflected or straight state shown in FIG. 1. For example, a baffle and/or straightening member may be provided in the wall of the inner shaft and/or a return pull wire may be provided in the wall of the inner shaft.

Figure 5:
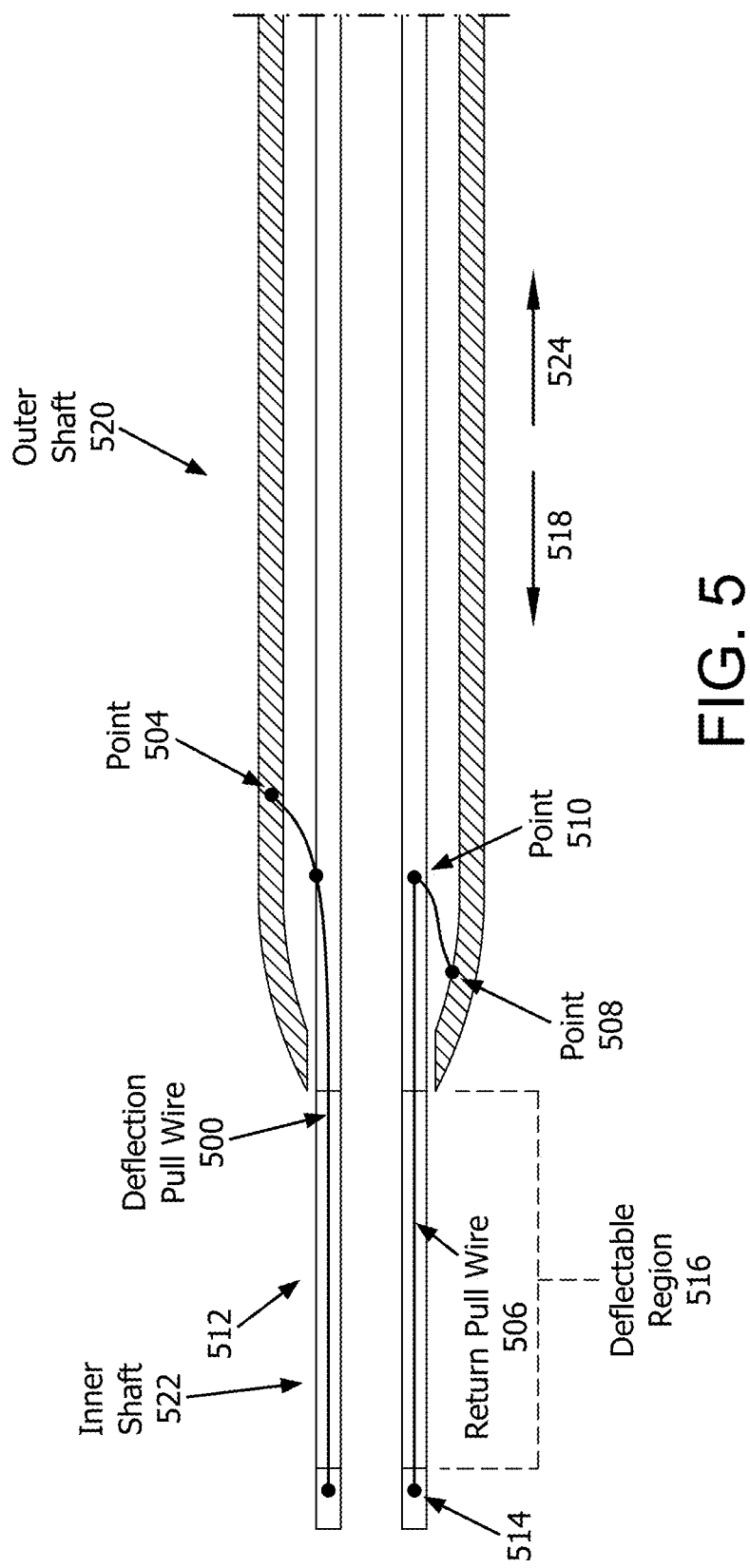
FIG. 5 provides an illustration showing another steerable sheath.
Figure 6:
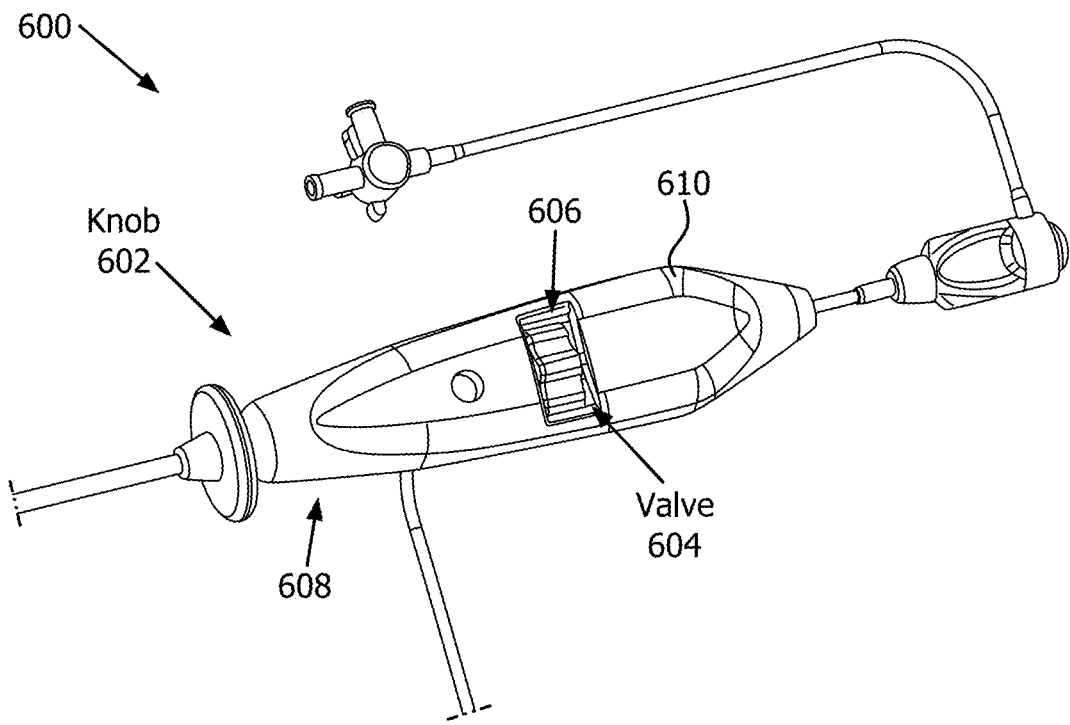
FIGS. 6-9 provide illustrations of a handle assembly for a steerable sheath.
Figure 7:
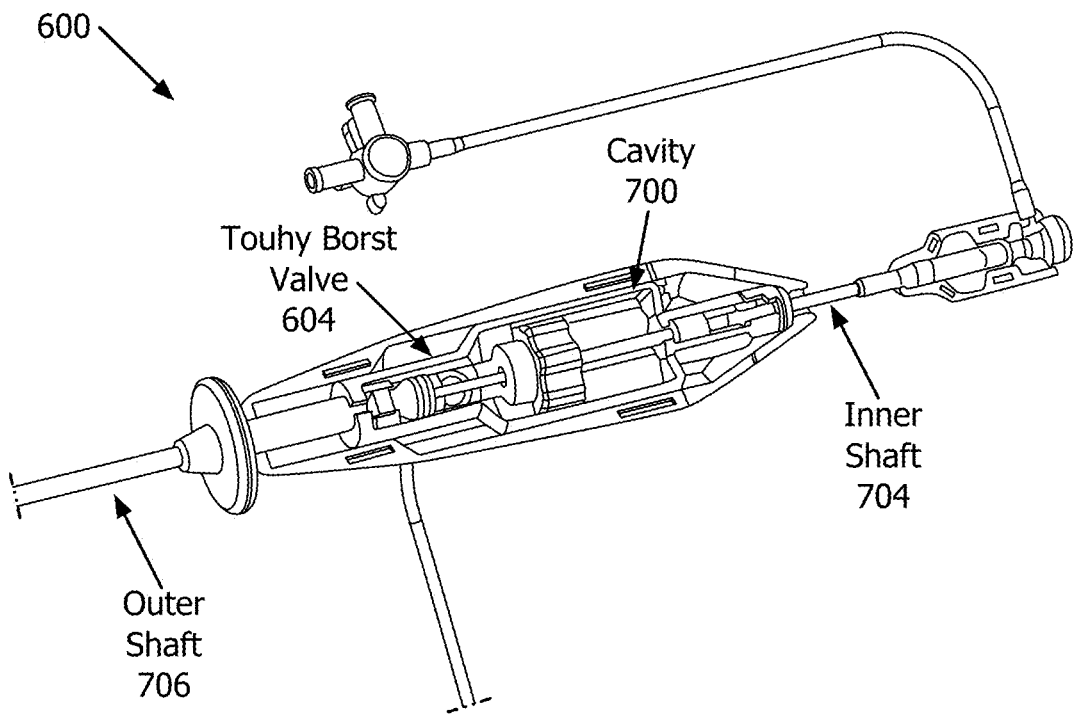

An illustration showing a steerable sheath with a return pull wire 506 is provided in FIG. 5. As shown in FIG. 5, the return pull wire 506 is disposed in the proximal portion 512 of the inner shaft 522. The return pull wire 506 is coupled to the inner shaft 522 at point 514, extends along a length of the deflectable region 516, exits the inner shaft at point 510, and is coupled to the outer shaft 520 at point 508. The return pull wire 506 is bent in direction 518 after exiting the inner shaft 522. As such, it's anchor point 508 is located closer to the deflectable region 516 than the anchor point 504 of the deflection pull wire 500. This arrangement of anchor points ensures that (i) there is slack in the return pull wire 506 when the inner shaft 522 is moved in direction 518 and (ii) there is slack in the deflection pull wire 500 when the inner shaft 522 is moved in direction 524. The slack in each wire 500, 506 means that the wire will not be engaged and pull the inner shaft in an unintended opposite direction.

The return pull wire 506 is shown in FIG. 5 as having the same or similar length as the deflection pull wire 500. The present solution is not limited in this regard. The return pull wire could alternatively be designed to travel the entire length of the inner shaft 522. The advantage of a short return pull wire is that it allows for a simplified handle mechanism because the requirement is just moving one tube in relation to another tube. This could be achieved, for example, via a push knob mechanism. The disadvantage of a short return pull wire is the exposure of another pull wire to the patient's blood and the potential of biocompatibility issues with the steerable sheath when used in certain situations. A relatively long return pull wire does not have these potential biocompatibility issues. However, the long return pull wire causes the handle mechanism to become more complex. Thus, the length of the pull wire is selected in accordance with a given application. Braids and/or coils may optionally be added to the proximal end of the inner shaft 522 to minimize the ability of the lumen to kink during operation of the steerable sheath.

Referring now to FIG. 6-9, there are provided illustrations for a handle assembly 600 that can be used with any of the steerable sheaths described above. The handle assembly 600 comprises a knob 602 to facilitate linear translation of the inner shaft 704 in relation to the outer shaft 706. The inner shaft 704 can be the same as or similar to inner shaft 102 of FIG. 1. The outer shaft 706 can be the same as or similar to outer shaft 104 of FIG. 1.

A proximal connection between the inner and outer shafts is a sliding connection that maintains hemostasis. The sliding connection is achieved via the integration of a valve 604 with the knob 602 in such a manner that the inner shaft 704 is able to slide relative to the outer shaft 706 and the knob's thumb geometry is located at a distal end 608 of the handle assembly 600. The valve 604 can include, but is not limited to, a touhy borst valve. The valve 604 is disposed in an internal cavity 700 of the knob 602. An aperture 606 is formed in a housing 610 of the knob 602 that allows a portion of the valve 604 to be exposed and/or accessible to a user of the steerable sheath. The exposed portion of the valve can be manipulated by a user to adjust an amount of sliding friction between the inner shaft and knob. The amount of inner shaft sliding friction translates to the amount of deflection and retention force. In effect, the handle assembly provides the steerable sheath with an adjustable deflection force.

Figure 8:
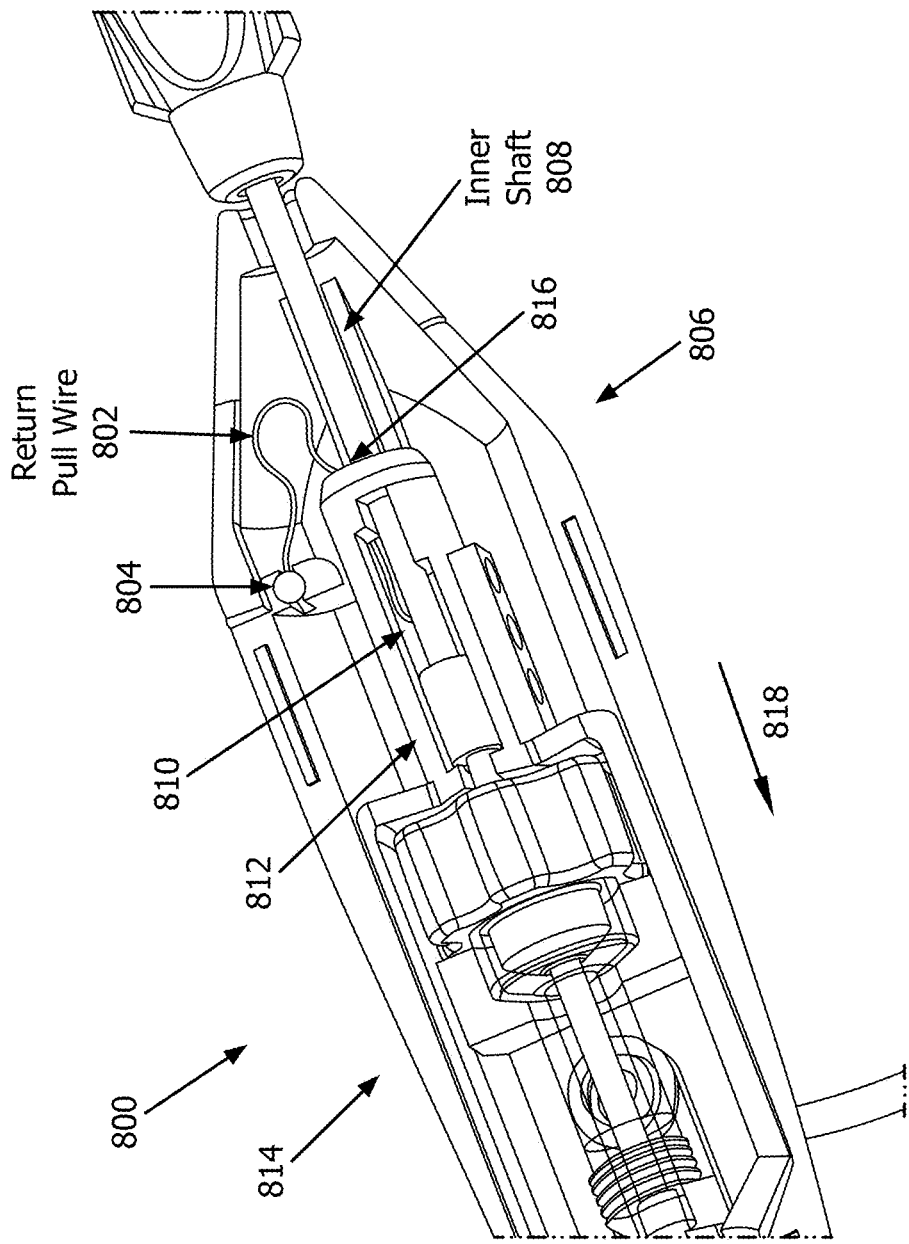
Figure 9:
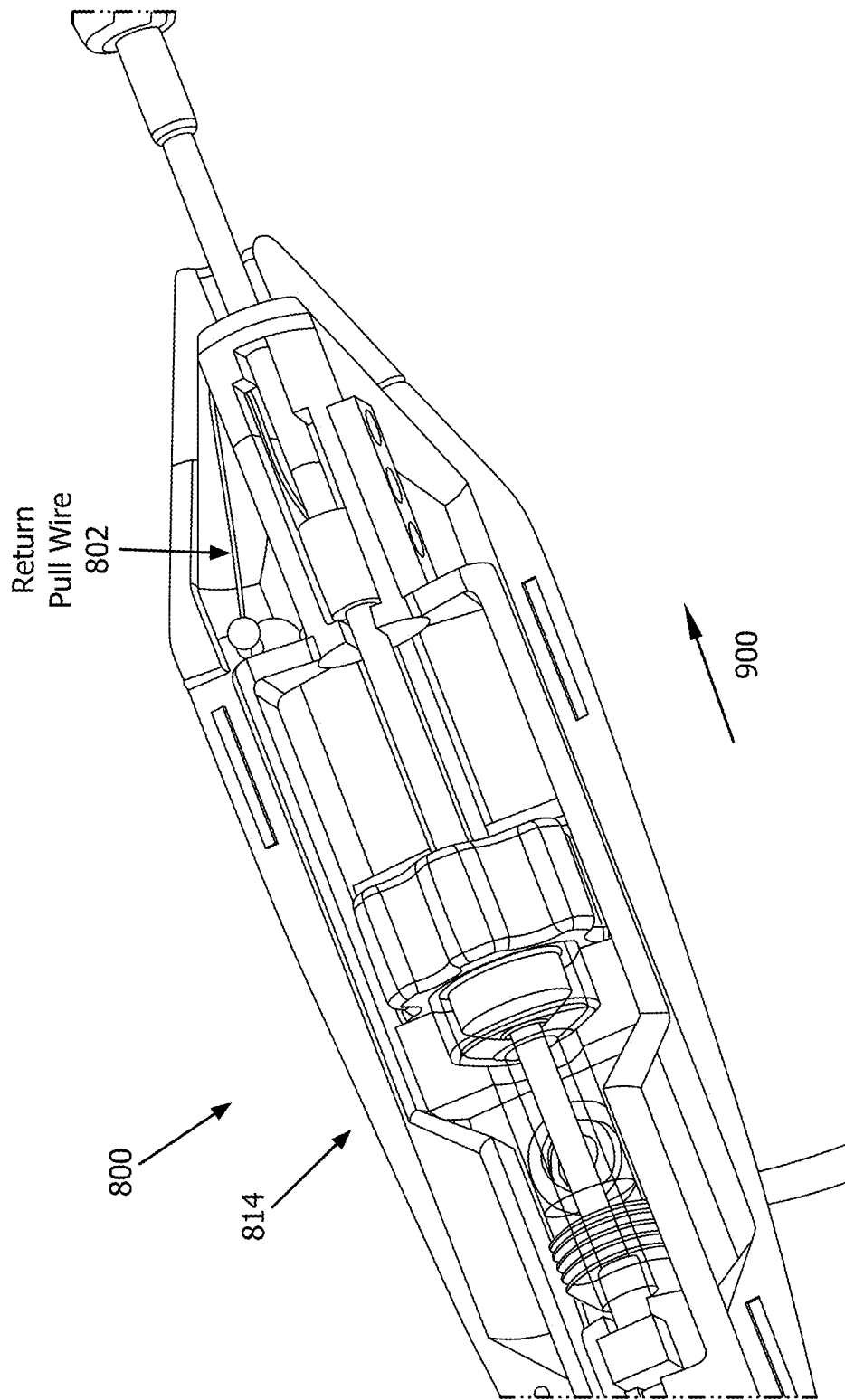

In some scenarios, a return pull wire is arranged to traverse an entire length of the inner shaft. FIGS. 8-9 provide illustrations showing a handle assembly 800 that can be used in these scenarios. The handle assembly 800 is similar to handle assembly 600 with the addition of a feature for engaging the return pull wire 802. The return pull wire 802 may be the same as or similar to return pull wire 506 of FIG. 5. The feature comprises a pin 804 located at a proximal end 806 of the handle assembly 800. The pin 804 is configured to facilitate tightening of the return pull wire 802.

The return pull wire 802 exits the inner shaft 808 at point 810, extends through an internal structure 812 of the knob 814, and exits the internal structure 812 at a point 816 located in the proximal end of the knob 814. When the knob 814 slides in direction 818 (because of the location of pin 804), there is slack in the return pull wire 802 as shown in FIG. 8. This slack ensures that engagement of the return pull wire 802 is avoided. Otherwise, if the return pull wire 802 were engaged when the inner shaft 808 is slid in direction 818, it would counteract the deflection pull wire and the deflection region of the inner shaft would not bend or otherwise deform.

When the knob 814 is moved in direction 900 to a most proximal position shown in FIG. 9, tension is applied to the return pull wire 802 whereby the return pull wire 802 straightens due to the removal of its slack. In effect, the deflection region of the inner shaft is straightened.

Figure 10:
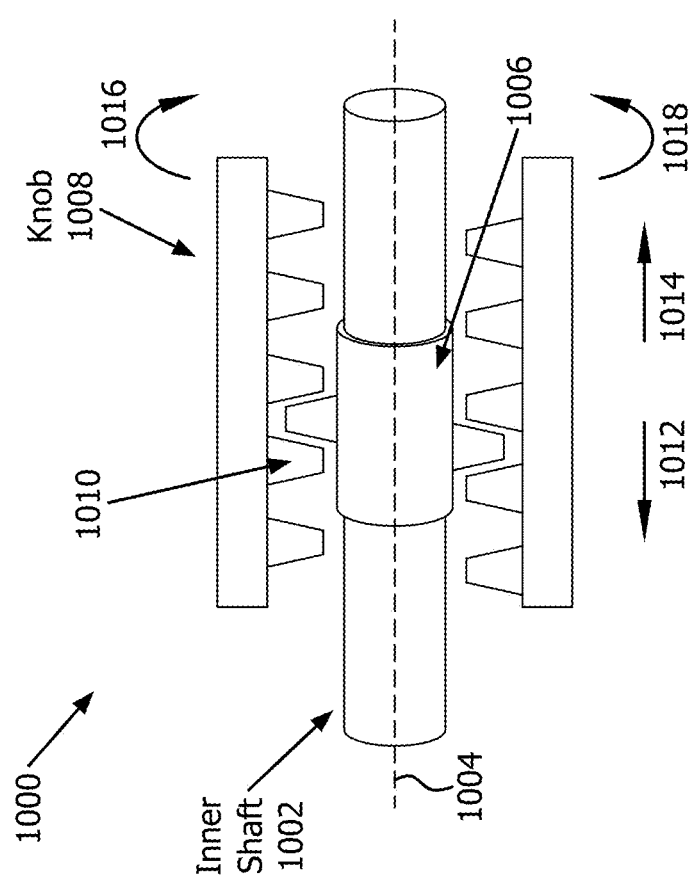
FIG. 10 provides an illustration for another handle assembly for the steerable sheath.

The present solution is not limited to the handle assembly shown in FIGS. 6-9. In other scenarios, the handle assembly comprises a threaded knob. An illustration of a threaded knob 1000 is provided in FIG. 10. The threaded knob 1000 extends along elongate length of the inner shaft 1002 and is rotatable about a central axis 1004 of the inner shaft 1002. The inner shaft 1002 is a component of a steerable sheath assembly. Other components (for example, the outer shaft) of the steerable sheath assembly are not shown in FIG. 10 for simplicity of illustration.

A coupler 1006 is securely disposed around the inner shaft 1002. The coupler 1006 is designed to engage thread(s) 1010 of the knob 1008. The coupler 1006 facilitates translation of the inner shaft 1002 in directions 1012, 1014 as the knob 1008 is rotated around axis 1004 in directions 1016, 1018. The present solution is not limited to the configuration shown in FIG. 10. Other mechanisms can be used to facilitate translation of the inner shaft in directions 1012, 1014 relative to an outer shaft.

Figure 11:
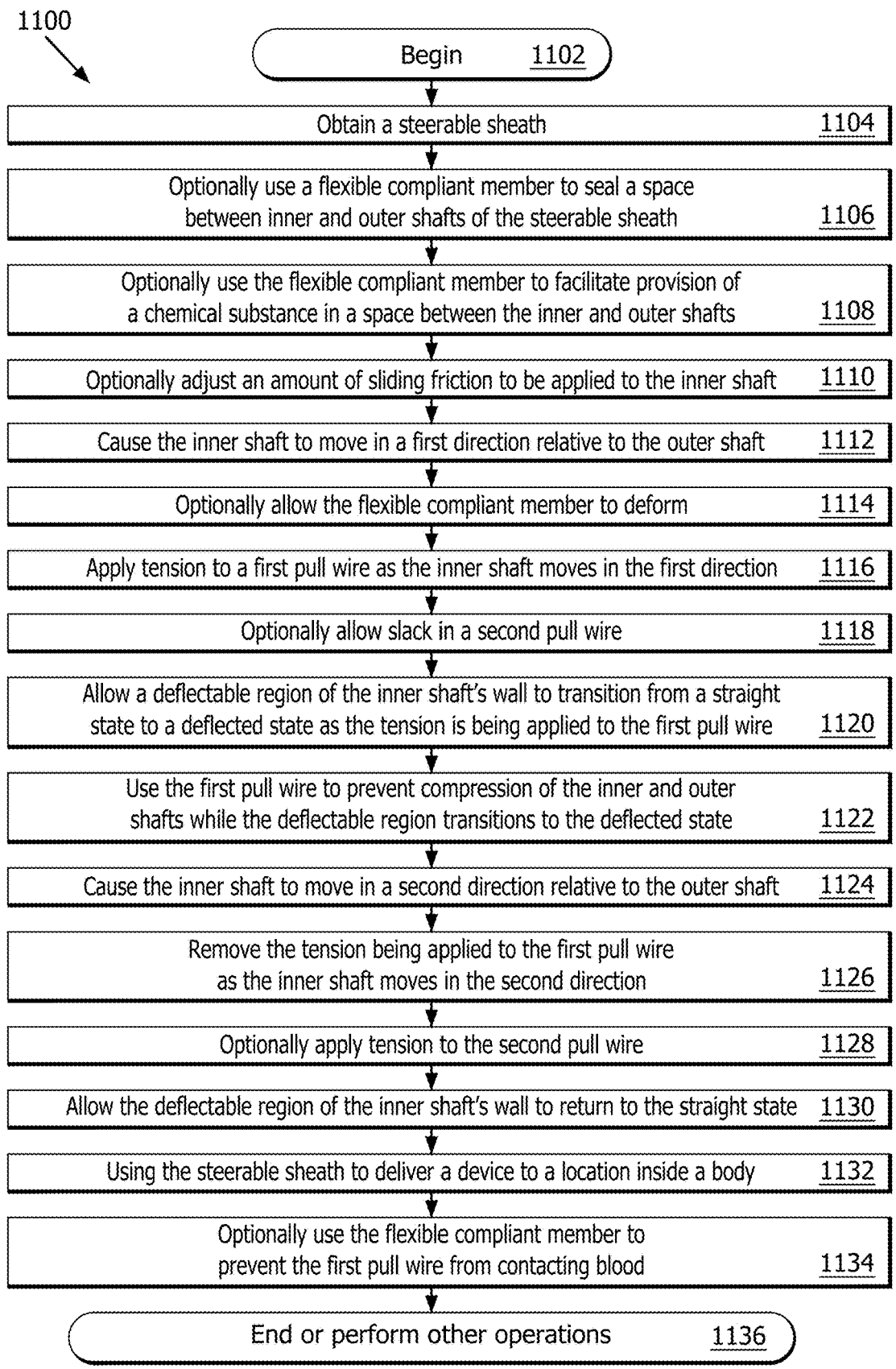
FIG. 11 provides a flow diagram of an illustrative method for operating a steerable sheath during a medical procedure.

Referring now to FIG. 11, there is provided a flow diagram of an illustrative method 1100 for operating a steerable sheath (for example, a steerable sheath 100 of FIG. 1) during a medical procedure. Method 1100 begins with 1102 and continues with 1104 where the steerable sheath is obtained. A flexible compliant member (for example, compliant member 300 of FIG. 3) is optionally used in 1106 to seal a space (for example, space 302 of FIG. 3) between inner and outer shafts (for example, shafts 102, 104 of FIG. 1) of the steerable sheath. The flexible compliant member may also optionally be used in 1108 to facilitate provision of a chemical substance in the space between the inner and outer shafts. The flexible compliant member extends between the inner shaft and the outer shaft.

In 1110, actions are optionally taken to adjust an amount of sliding friction to be applied to the inner shaft. This adjustment can be achieved via manipulation of a valve (for example, valve 604 of FIG. 6) disposed in a knob (for example, knob 602 of FIG. 6) of a handle assembly (for example, handle assembly 600 of FIG. 6) being used with the steerable sheath. The sliding friction adjustment translates to an amount of force required for causing deflection of a deflectable region (for example, deflectable region 110 of FIG. 1) of the inner shaft's wall (for example, the wall defining lumen 126 of FIG. 1).

In 1112, the inner shaft of the steerable sheath is caused to move in a first direction (for example, direction 120 of FIG. 1) relative to the outer shaft. The outer shaft has a lumen (for example, lumen 116 of FIG. 1) in which the inner shaft is at least partially disposed. The inner shaft may be caused to move in the first direction via application of a pushing force to the knob of the handle assembly coupled to the steerable sheath.

As the inner shaft moves (i) the flexible compliant member is allowed to deform as shown by 1114, (ii) tension is applied to a first pull wire (for example, pull wire 112 of FIG. 1) as shown by 1116, and/or (iii) slack is allowed in a second pull wire (for example, return pull wire 506 of FIG. 5) as shown by 1118. The first pull wire is partially disposed in a wall of the inner shaft and partially disposed in the lumen (for example, lumen 116 of FIG. 1) of the outer shaft.

In some scenarios, a first end (for example, end 148 of FIG. 1) of the first pull wire is connected to the inner shaft and a second end (for example, end 146 of FIG. 1) of the first pull wire being connected to the outer shaft. The first pull wire may extend only a portion of an entire length of the inner shaft that comprises at least the deflectable region. The second pull wire is partially disposed in the wall of the inner shaft and partially disposed in the first lumen of the outer shaft. A first end of the second pull wire is connected to the inner shaft and a second end of the second pull wire is connected to the outer shaft. A point at which the second pull wire is coupled to the outer shaft is closer to the deflectable region of the inner shaft's wall than a point at which the first pull wire is coupled to the outer shaft. The second pull wire extends through the deflectable region of the inner shaft's wall. The first and second pull wires have a same length or different length. In the latter case, the second pull wire may extend an entire length of the inner shaft.

The tension can be applied in 1116 by changing a distance between a first point where the first pull wire exits the inner shaft's wall relative to a second point where the second end of the first pull wire is connected to the outer shaft. The distance can be changed by moving a location of a first point where the first pull wire exits the inner shaft's wall relative to a second point where the second end of the first pull wire is connected to the outer shaft. The second point has a static location relative to the outer shaft throughout use of the steerable sheath.

In 1120, the deflectable region of the inner shaft's wall is allowed to transition from a straight state (for example, as shown in FIG. 1) to a deflected state (for example, as shown in FIG. 2) as the tension is being applied to the first pull wire. A material of the deflectable region of the inner shaft may have a durometer that is lower than a durometer of a material of a remaining portion of the inner shaft such that the remaining portion of the inner shaft remains in a straight state throughout use of the steerable sheath. The first pull wire is used in 1122 to prevent compression of the inner and outer shafts while the deflectable region transitions to the deflected state.

In 1124, the inner shaft is caused to move in a second direction (for example, second direction 122 of FIG. 1) relative to the outer shaft. The tension is removed from the first pull wire in 1126 as the inner shaft moves in the second direction. Tension is optionally applied to the second pull wire in 1128 as the inner shaft moves in the second direction. The deflectable region of the inner shaft is allowed to return to the straight state in 1130 as the tension is being removed from the first pull wire.

In 1132, the steerable sheath is used to deliver a device (for example, catheter 160 of FIG. 1) to a location inside a body of a living thing during the medical procedure. The device is movably disposed in a second lumen (for example, lumen 126 of FIG. 1) of the inner shaft. The flexible compliant member is optionally used in 1134 to prevent the first pull wire and/or the second pull wire from contacting blood of the living thing. Subsequently, 1136 is performed where method 1100 ends or other operations are performed.

Although the present solution has been illustrated and described with respect to one or more implementations, equivalent alterations and modifications will occur to others skilled in the art upon the reading and understanding of this specification and the annexed drawings. In addition, while a particular feature of the present solution may have been disclosed with respect to only one of several implementations, such feature may be combined with one or more other features of the other implementations as may be desired and advantageous for any given or particular application. Thus, the breadth and scope of the present solution should not be limited by any of the above described embodiments. Rather, the scope of the present solution should be defined in accordance with the following claims and their equivalents.

What is claimed is:

1. A method for operating a steerable sheath during a medical procedure, comprising:
    causing an inner shaft of the steerable sheath to move in a first direction relative to an outer shaft having a first lumen in which the inner shaft is at least partially disposed, wherein the causing the inner shaft of the steerable sheath to move in the first direction comprises applying a force to a knob;
    applying tension to a first pull wire as the inner shaft moves in the first direction, the first pull wire being partially disposed in a wall of the inner shaft and partially disposed in the first lumen of the outer shaft, a first end of the first pull wire being connected to the inner shaft and a second end of the first pull wire being connected to the outer shaft;
    allowing a deflectable region of the inner shaft's wall to transition from a straight state to a deflected state as the tension is being applied to the first pull wire;
    causing the inner shaft of the steerable sheath to move in a second opposing direction relative to the outer shaft;
    removing the tension being applied to the first pull wire as the inner shaft moves in the second opposing direction;
    allowing the deflectable region of the inner shaft's wall to return to the straight state as the tension is being removed from the first pull wire; and
    adjusting an amount of sliding friction between the inner shaft and the knob via manipulation of a valve disposed in the knob.

2. The method according to claim 1, further comprising using the steerable sheath to deliver a device to a location inside a body of a living thing during the medical procedure, wherein the device is movably disposed in a second lumen of the inner shaft.

3. The method according to claim 1, wherein a material of the deflectable region of the inner shaft has a durometer that is lower than a durometer of a material of a remaining portion of the inner shaft such that the remaining portion of the inner shaft remains in a straight state throughout use of the steerable sheath.

4. The method according to claim 1, wherein the first pull wire extends only a portion of an entire length of the inner shaft that comprises at least the deflectable region.

5. The method according to claim 1, further comprising using the first pull wire to prevent compression of the inner shaft and the outer shaft while the deflectable region transitions to the deflected state.

6. The method according to claim 1, wherein the applying tension to a first pull wire comprises changing a location of a first point where the first pull wire exits the inner shaft's wall relative to a second point where the second end of the first pull wire is connected to the outer shaft.

7. The method according to claim 6, wherein the second point has a static location relative to the outer shaft throughout use of the steerable sheath.

8. The method according to claim 1, wherein applying tension to a first pull wire comprises changing a distance between a first point where the first pull wire exits the inner shaft's wall relative to a second point where the second end of the first pull wire is connected to the outer shaft.

9. The method according to claim 1, further comprising using a flexible compliant member to seal a space between the inner shaft and the outer shaft, the flexible compliant member extending between the inner shaft and the outer shaft.

10. The method according to claim 9, further comprising allowing the flexible compliant member to deform as the inner shaft moves in the first direction and tension is being applied to the first pull wire.

11. The method according to claim 9, further comprising using the flexible compliant member to prevent the first pull wire from contacting blood of an individual to which the medical procedure is being performed.

12. The method according to claim 9, further comprising using the flexible compliant member to facilitate provision of a chemical substance in a space between the inner shaft and the outer shaft.

13. The method according to claim 1, further comprising allowing slack in a second pull wire when the tension is being applied to the first pull wire, the second pull wire being partially disposed in the wall of the inner shaft and partially disposed in the first lumen of the outer shaft, a first end of the second pull wire being connected to the inner shaft and a second end of the second pull wire being connected to the outer shaft.

14. The method according to claim 13, wherein a point at which the second pull wire is coupled to the outer shaft is closer to the deflectable region of the inner shaft's wall than a point at which the first pull wire is coupled to the outer shaft.

15. The method according to claim 13, wherein the second pull wire extends through the deflectable region of the inner shaft's wall.

16. The method according to claim 13, further comprising applying tension to the second pull wire as the inner shaft moves in the second opposing direction.

17. The method according to claim 13, wherein the first and second pull wires have a same length or different length.

18. The method according to claim 13, wherein the second pull wire extends an entire length of the inner shaft.

19. A method for operating a steerable sheath during a medical procedure, comprising:
causing an inner shaft of the steerable sheath to move in a first direction relative to an outer shaft having a first lumen in which the inner shaft is at least partially disposed, wherein the causing the inner shaft of the steerable sheath to move in the first direction comprises applying a force to a knob;
applying tension to a first pull wire as the inner shaft moves in the first direction, the first pull wire being partially disposed in a wall of the inner shaft and partially disposed in the first lumen of the outer shaft, a first end of the first pull wire being connected to the inner shaft and a second end of the first pull wire being connected to the outer shaft;
allowing a deflectable region of the inner shaft's wall to transition from a straight state to a deflected state as the tension is being applied to the first pull wire;
causing the inner shaft of the steerable sheath to move in a second opposing direction relative to the outer shaft;
removing the tension being applied to the first pull wire as the inner shaft moves in the second opposing direction;
allowing the deflectable region of the inner shaft's wall to return to the straight state as the tension is being removed from the first pull wire; and
adjusting an amount of force required for causing deflection of the deflectable region of the inner shaft's wall via manipulation of a valve disposed in the knob.

20. A steerable sheath, comprising:
an outer shaft having a first lumen;
an inner shaft at least partially disposed in the first lumen, configured to move in a first direction relative to an outer shaft, and configured to move in a second opposing direction relative to the outer shaft; and
a first pull wire configured to have tension applied thereto as the inner shaft moves in the first direction, wherein the first pull wire is partially disposed in a wall of the inner shaft and partially disposed in the first lumen of the outer shaft, a first end of the first pull wire is connected to the inner shaft, and a second end of the first pull wire is connected to the outer shaft;
wherein a deflectable region of the inner shaft's wall is transitionable from a straight state to a deflected state as the tension is being applied to the first pull wire;
wherein the deflectable region of the inner shaft's wall is configured to return to the straight state as the tension is being removed from the first pull wire when the inner shaft moves in the second opposing direction;
wherein movement of the inner shaft in the first direction is caused by applying a force to a knob; and
wherein an amount of sliding friction between the inner shaft and the knob is adjustable via manipulation of a valve disposed in the knob.

21. The steerable sheath according to claim 20, wherein the steerable sheath is configured to deliver a device to a location inside a body of a living thing during a medical procedure, wherein the device is movably disposed in a second lumen of the inner shaft.

22. The steerable sheath according to claim 20, wherein a material of the deflectable region of the inner shaft has a durometer that is lower than a durometer of a material of a remaining portion of the inner shaft such that the remaining portion of the inner shaft remains in a straight state throughout use of the steerable sheath.

23. The steerable sheath according to claim 20, wherein the first pull wire extends only a portion of an entire length of the inner shaft that comprises at least the deflectable region.

24. The steerable sheath according to claim 20, wherein the first pull wire is configured to prevent compression of the inner shaft and the outer shaft while the deflectable region transitions to the deflected state.

25. The steerable sheath according to claim 20, wherein the tension is applied to the first pull wire by changing a location of a first point where the first pull wire exits the inner shaft's wall relative to a second point where the second end of the first pull wire is connected to the outer shaft.

26. The steerable sheath according to claim 25, wherein the second point has a static location relative to the outer shaft throughout use of the steerable sheath.

27. The steerable sheath according to claim 20, wherein the tension is applied to the first pull wire by changing a distance between a first point where the first pull wire exits the inner shaft's wall relative to a second point where the second end of the first pull wire is connected to the outer shaft.

28. The steerable sheath according to claim 20, further comprising a flexible compliant member configured to seal a space between the inner shaft and the outer shaft, the flexible compliant member extending between the inner shaft and the outer shaft.

29. The steerable sheath according to claim 28, wherein the flexible compliant member is further configured to deform as the inner shaft moves in the first direction and tension is being applied to the first pull wire.

30. The steerable sheath according to claim 28, wherein the flexible compliant member is further configured to prevent the first pull wire from contacting blood of an individual to which a medical procedure is being performed.

31. The steerable sheath according to claim 28, wherein the flexible compliant member is further configured to facilitate provision of a chemical substance in a space between the inner shaft and the outer shaft.

32. The steerable sheath according to claim 20, further comprising a second pull wire that is configured to have slack when the tension is being applied to the first pull wire, the second pull wire being partially disposed in the wall of the inner shaft and partially disposed in the first lumen of the outer shaft, a first end of the second pull wire being connected to the inner shaft and a second end of the second pull wire being connected to the outer shaft.

33. The steerable sheath according to claim 32, wherein a point at which the second pull wire is coupled to the outer shaft is closer to the deflectable region of the inner shaft's wall than a point at which the first pull wire is coupled to the outer shaft.

34. The steerable sheath according to claim 32, wherein the second pull wire extends through the deflectable region of the inner shaft's wall.

35. The steerable sheath according to claim 32, wherein tension is applied to the second pull wire as the inner shaft moves in the second opposing direction.

36. The steerable sheath according to claim 32, wherein the first and second pull wires have a same length or different length.

37. The steerable sheath according to claim 32, wherein the second pull wire extends an entire length of the inner shaft.

38. A steerable sheath, comprising:
an outer shaft having a first lumen;
an inner shaft at least partially disposed in the first lumen, configured to move in a first direction relative to an outer shaft, and configured to move in a second opposing direction relative to the outer shaft; and
a first pull wire configured to have tension applied thereto as the inner shaft moves in the first direction, wherein the first pull wire is partially disposed in a wall of the inner shaft and partially disposed in the first lumen of the outer shaft, a first end of the first pull wire is connected to the inner shaft, and a second end of the first pull wire is connected to the outer shaft;
wherein a deflectable region of the inner shaft's wall is transitionable from a straight state to a deflected state as the tension is being applied to the first pull wire;
wherein the deflectable region of the inner shaft's wall is configured to return to the straight state as the tension is being removed from the first pull wire when the inner shaft moves in the second opposing direction;
wherein movement of the inner shaft in the first direction is caused by applying a force to a knob; and
wherein an amount of force required for causing deflection of the deflectable region of the inner shaft's wall is adjustable via manipulation of a valve disposed in the knob.

* * * * *